United States Patent
Pulst et al.

(12) 
(10) Patent No.: US 6,194,171 B1
(45) Date of Patent: Feb. 27, 2001

(54) NUCLEIC ACIDS ENCODING ATAXIN-2 BINDING PROTEINS

(75) Inventors: Stefan M. Pulst; Hiroki Shibata, both of Los Angeles, CA (US)

(73) Assignee: Cedard-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/145,391

(22) Filed: Sep. 1, 1998

(51) Int. Cl.[7] .............................. C12P 21/02; C12N 1/00; C12N 5/10; C12N 15/12; C12N 15/63

(52) U.S. Cl. ................. 435/69.1; 435/243; 435/320.1; 435/325; 435/410; 536/23.5

(58) Field of Search ..................... 536/23.5; 435/320.1, 435/243, 325, 420, 69.1

(56) References Cited

U.S. PATENT DOCUMENTS 5,714,594   2/1998   Weinshilboum et al. .

FOREIGN PATENT DOCUMENTS

WO97/42314   11/1997   (WO) .

OTHER PUBLICATIONS

Berendsen, Science, vol. 282: pp. 642–643, Oct. 1998.*
Hillier et al., "zx61d04.sl Soares total fetus Nb2HF8 9w Homo sapiens cDNA clone 795943 3' similar to TR:G608464 Ribonucleoprotein," *EMBL* HS1255920, Jun. 1997.
Pulst et al., "Spinocerebellar ataxia type 2 (SCA2): binding proteins, subcellular localization and post–transitional processing," *Neurology* 50:A309–A310 (1998).
Cancel et al., "Molecular and clinical correlations in spinocerebellar ataxia 2: a study of 32 families," *Hum. Mol. Gen.* 6:709–715 (1997).
Imbert et al, "Cloning of the gene for spinocerebellar ataxia 2 reveals a locus with high sensitivity to expanded CAG/glutamine repeats," *Nat. Genet.* 14:285–291 (1996).
Klockgether and Dichgans, "Trinucleotide repeats and hereditary ataxias," *Nat. Med.* 3:149–150 (1997).
Koshy et al., "Spinocerebellar ataxia type–1 and spinobulbar muscular atrophy gene products interact with glyceraldehyde–3–phosphate dehydrogenase," *Hum. Mol. Gen.* 5:1311–1318 (1996).
Lorenzetti et al., "The expansion of the CAG repeat in ataxin–2 is a frequent cause of autosomal dominant spinocerebellar ataxia," *Am. Acad. Neur.* 49:1009–1013 (1997).
Matilla et al., "The cerebellar leucine–rich acidic nuclear protein interacts with ataxin–1," *Nature* 389:974–978 (1997).
Matsuoka et al., "A nuclear factor containing the leucine–rich repeats expressed in murine cerebellar neurons," *Proc. Natl. Acad. Sci. USA* 91:9670–9674 (1994).
Mérel et al., "Screening for germ–line mutations in the NF2 gene," *Genes, Chromosomes & Cancer* 12:117–127 (1995).
Pulst et al., "Moderate expansion of a normally biallelic trinucleotide repeat in spinocerebellar ataxia type 2," *Nat. Genet.* 14:269–276 (1996).
Skinner et al., "Ataxin–1 with an expanded glutamine tract alters nuclear matrix–associated structures," *Nature* 389:971–974 (1997).
Trottier et al., "Polyglutamine expansion as a pathological epitope in Huntington's disease and four dominant cerebellar ataxias," *Nature* 378:403–406 (1995).

\* cited by examiner

*Primary Examiner*—Terry McKelvey
(74) *Attorney, Agent, or Firm*—Campbell & Flores LLP

(57) ABSTRACT

In accordance with the present invention, there are provided novel isolated nucleic acids encoding ataxin-2-binding proteins (A2BPs), functional fragments thereof, vectors containing invention nucleic acids and recombinant cells transformed therewith, antisense-nucleic acids thereto. Also provided are novel isolated ataxin-2-binding proteins (A2BPs) having ability to bind to ataxin-2, methods for expression of A2BP, transgenic non-human mammals that express invention A2BP, anti-A2BP antibodies, and methods related thereto.

16 Claims, 4 Drawing Sheets

NUCLEIC ACIDS ENCODING ATAXIN-2 BINDING PROTEINS

The present invention relates to molecular biology and more specifically to nucleic acids and the proteins encoded by them. Invention nucleic acids encode novel ataxin-2 binding proteins. The invention also relates to methods for making and using such nucleic acids and proteins, for example, to treat particular pathologies.

BACKGROUND OF THE INVENTION

Numerous pathologies characterized by abnormal or undesirable cell death or cell growth are the result of abnormal gene expression or activity. Cellular degenerative and hyperproliferative disorders such as Alzheimer's disease and cancer are two particular examples. Although several genes that contribute to degenerative and hyperproliferative disorders have been identified, the signal transduction pathways which mediate the development of such disorders presently are not well understood.

Spinocerebellar ataxia type-2 is one example of a group of clinically similar late onset hereditary degenerative disorders affecting the brain and central nervous system. A single gene SCA2, located on chromosome 12, has been linked to development of spinocerebellar ataxia type-2; SCA2 encodes ataxin-2, a 140 kDa protein whose function is presently unknown. Clinically similar neurodegenerative disorders include, for example, spinocerebellar ataxia types 1 and 6, spinobulbar muscular atrophy, Huntington disease and Machado-Joseph disease (Trottier et al., Nature378:403–406 (1995)). Although the development of these similar disorders are mediated by distinct genes, a shared genetic alteration initiates onset of the pathologies. In the case of spinocerebellar ataxia type-2, for example, afflicted individuals exhibit expansion of a CAG trinucleotide in SCA2 and a corresponding increase in the number of glutamine residues in the encoded ataxin-2 protein (Pulst et al., Nat. Genet. 14:269–276 (1996)). Typically, afflicted individuals have a polyglutamine sequence of about 35–39 residues, whereas normal individuals have about 22 contiguous glutamine residues in ataxin-2. Similarly, CAG repeat expansion in genes linked to spinocerebellar ataxia types 1 and 6, spinobulbar muscular atrophy, Huntington's disease and Machado-Joseph disease correlate with the development of these disorders. As a result of this shared genetic alteration, these pathologies are collectively referred to as glutamine repeat disorders.

In spite of this genetic knowledge, the function of genes, such as SCA2 in general, and the role of CAG repeat expansion and corresponding glutamine sequence expansion in the development of degenerative disorders such as spinocerebellar ataxia type-2 in particular, is not understood. In this regard, the glutamine repeat sequence of SCA3 in normal individuals is in the same size range as that of the glutamine repeat sequence of SCA2 in individuals afflicted with spinocerebellar ataxia type-2. Similarly, the molecular components that regulate or mediate cellular degeneration, and the mechanism by which they participate in this signal transduction pathway, are not understood.

Thus, a need exists to identify and characterize the molecular components that participate in this signal transduction pathway, such as proteins that bind to ataxin-2 in vivo. Moreover, a need exists to identify the nucleic acid and amino acid sequences of the respective genes and gene products, their activities, and the functional domains of such binding proteins. To the extent that such molecules are identified, they can form the basis for the development of diagnostic protocols or clinical therapies useful for the diagnosis or treatment of disorders characterized by cellular degeneration or hyperproliferation. The present invention satisfies this need and provides related advantages as well.

SUMMARY OF THE INVENTION

In accordance with the present invention, there are provided novel isolated nucleic acids encoding ataxin-2-binding proteins (A2BPs), or functional fragments thereof. The invention also provides vectors containing invention nucleic acids and recombinant cells transformed therewith, antisense-nucleic acids thereto and related compositions. Further provided are oligonucleotides capable of hybridizing with an invention nucleic acid, such oligonucleotides further being labeled. Invention nucleic acids described herein are useful as probes for assaying an amount of A2BP mRNA in a sample and for identifying nucleic acids encoding a A2BP. Invention nucleic acids also are useful for expression in cells for the purposes of identifying agonists or antagonists of A2BP function.

In accordance with the present invention, also provided are novel isolated ataxin-2-binding proteins (A2BPs) having ability to bind to ataxin-2 or having ability to bind to a nucleic acid molecule. Methods for expression of A2BP or functional fragments thereof additionally are provided. Proteins or fragments thereof are useful in bioassays, as therapeutic compositions, and as immunogens for producing anti-A2BP antibodies. Also provided are transgenic non-human mammals that express invention A2BP and mutants thereof. Transgenic non-human mammals that do not express an endogenous A2BP additionally are provided.

Antibodies having specific reactivity with A2BP also are provided. These antibodies are useful for detecting A2BP in a sample in diagnostic assays, or for identifying genes encoding proteins having similar immunoreactivity to A2BP. Invention antibodies also can be used to purify a A2BP from biological fluid, tissues, cells, and the like.

Methods for identifying A2BP binding proteins also are provided. A method comprises contacting a sample containing a A2BP binding protein and identifying the protein that binds thereto. Also provided are methods for identifying a nucleic acid molecule that binds to A2BP. A method comprises contacting a sample containing nucleic acids and identifying a nucleic acid molecule that binds thereto.

Methods for modulating the activity of a protein or RNA that binds A2BP also are provided. A method comprises contacting a A2BP binding protein or nucleic acid molecule with a substantially pure A2BP, or functional fragment thereof. A method of modulating the activity of ataxin-2 also is provided.

Methods of treating a degenerative or hyperproliferative disorder are provided. A method of the invention employs an antisense A2BP nucleic acid in an amount effective to inhibit expression of a human 2BP. A method also employs A2BP or functional fragment thereof or agonists or antagonists thereto administered to a subject.

DETAILED DESCRIPTION OF THE INVENTION

Figure 1:
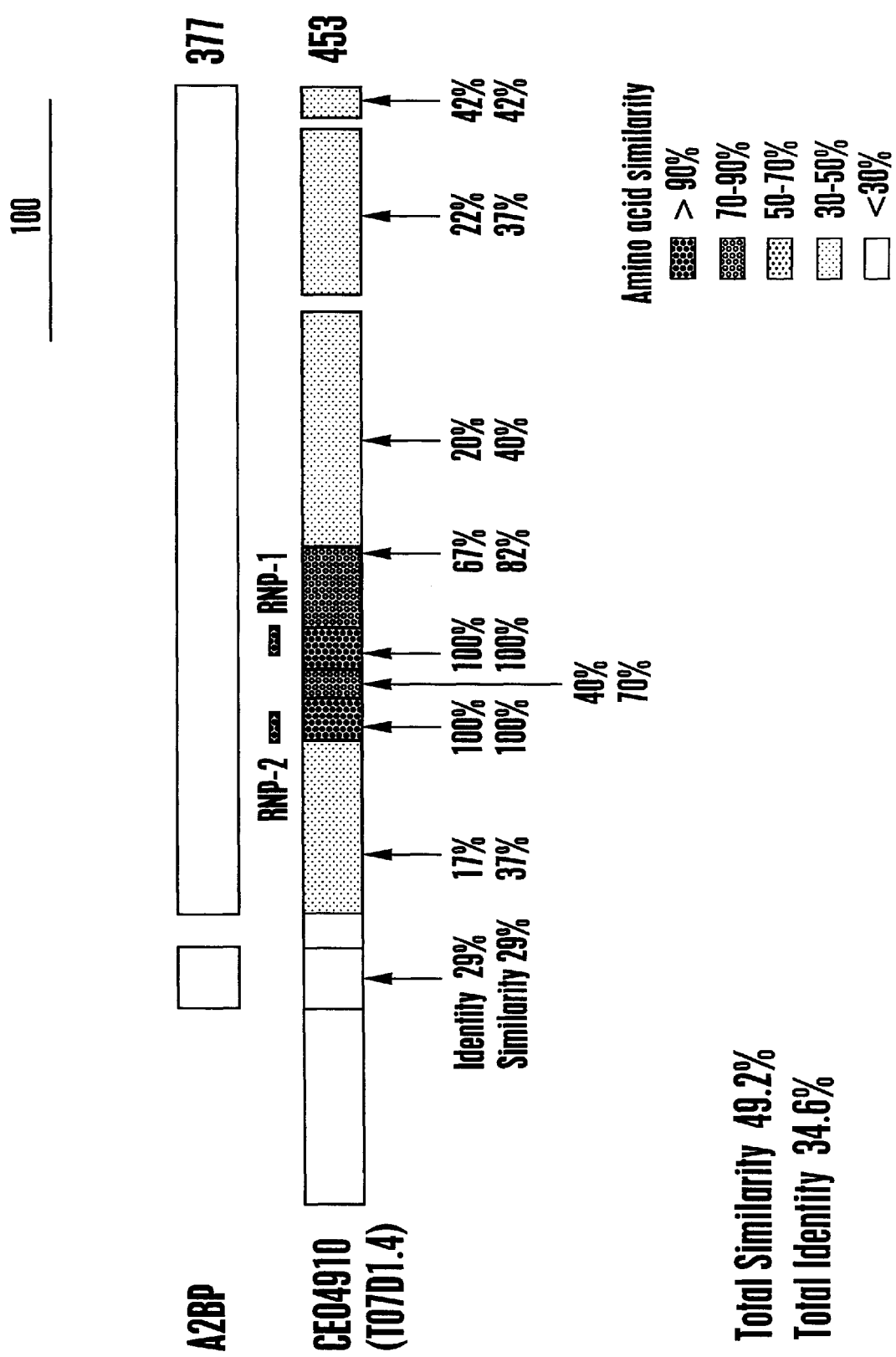
FIG. 1 shows a diagram of the amino acid sequence similarity and identity between an invention A2BP and the CE04910 nematode homologue.

In accordance with the present invention, there are provided isolated nucleic acids, which encode novel mammalian ataxin-2 binding proteins (A2BPs), and functional fragments thereof. As used herein, invention A2BPs are those that have the ability to bind, preferably in vivo, to at least one form of a ataxin-2 protein encoded by a SCA2 gene, ataxin-2 like proteins, or to a nucleic acid molecule. The term "A2BP" refers to substantially pure native A2BP, or recombinantly produced proteins, including naturally occurring allelic variants thereof such as mRNA generated by alternative splicing of a primary transcript, fragments thereof which retain at least one native biological activity, including an ability to bind to ataxin-2, an ability to bind to a nucleic acid molecule, or having immunogenicity. In another embodiment, A2BPs referred to herein, are those polypeptides specifically recognized by an antibody that also specifically recognizes a A2BP (preferably human) including an amino acid sequence set forth in SEQ ID NO:2. Invention isolated A2BPs are free of cellular components or contaminants normally associated with a native in vivo environment.

The invention nucleic acid molecules described herein can be useful, for example, to produce invention proteins, when such nucleic acids are incorporated into a variety of expression systems known to those of skill in the art. In addition, invention nucleic acid molecules or fragments thereof can be labeled with a detectable label and used as hybridization probes for assaying for the presence or amount of an invention A2BP gene or mRNA in a given sample, for example. The nucleic acid molecules and fragments thereof described herein also are useful as primers or templates in a PCR reaction for amplifying genes encoding invention proteins described herein.

The term "nucleic acid", also referred to as a polynucleotide, oligonucleotide or primer, encompasses ribonucleic acid (RNA) and deoxyribonucleic acid (DNA) which can be double or single stranded. RNA can be unspliced or spliced (i.e. mRNA), tRNA or rRNA and DNA can be complementary DNA (cDNA) or genomic DNA, such as a nucleic acid encoding an A2BP polypeptide, or an antisense thereto.

Use of the terms "isolated" or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

One means of isolating a nucleic acid encoding a A2BP polypeptide is to screen a nucleic acid library with a natural or artificially designed probe (e.g., DNA, antibody and the like) using methods well known in the art (see, for example, Sambrook et al., *Molecular Cloning. A Laboratory Manual*, Cold Spring Harbor Laboratory Press, 1989). DNA probes derived from mammalian A2BP gene are particularly useful for this purpose. DNA and cDNA molecules that encode A2BP polypeptides can be used to obtain complementary genomic DNA, cDNA or RNA from mammalian (e.g., human, monkey, mouse, rat, rabbit, pig, cow, and the like), other animal sources, or to isolate related cDNA or genomic clones by the screening of cDNA or genomic libraries, by methods described in more detail below. Examples of such nucleic acids are RNA, cDNA, or isolated genomic DNA encoding an A2BP polypeptide. Such nucleic acids include, but are not limited to, nucleic acids comprising substantially the same nucleotide sequence as set forth in SEQ ID No:1.

As used herein, "mammalian" refers to a variety of species from which an invention A2BP is derived, e.g., human, rat, mouse, rabbit, monkey, baboon, bovine, porcine, ovine, canine, feline, and the like. A preferred A2BP herein, is human A2BP.

In one embodiment, invention nucleic acids comprise substantially the same nucleotide sequence as set forth in SEQ ID NO:1. In another embodiment, invention nucleic acid molecules encoding A2BPs comprise substantially the same nucleotide sequence as nucleotides 1987–1979 of SEQ ID NO:1. Preferred nucleic acid molecule cDNAs encoding the invention proteins comprise the same nucleotide sequence as nucleotides 1987–1979 of SEQ ID NO:1.

As used herein, "substantially the same" in reference to a nucleotide sequence means a nucleic acid having sufficient identity to the reference polynucleotide such that it will hybridize to the reference nucleotide under moderately stringent hybridization conditions (i.e. conditions under which polynucleic acid hybrids are stable). In one embodiment, a DNA sequence having substantially the same nucleotide sequence as the reference nucleotide sequence encodes substantially the same amino acid sequence as that set forth in SEQ ID NO:1. In another embodiment, a DNA sequence having substantially the same nucleotide sequence as the reference nucleotide sequence has at least 60% identity with respect to the reference nucleotide sequence. DNA having at least 70%, more preferably at least 90%, yet more preferably at least 95% identity to the reference nucleotide sequence is preferred.

This invention also encompasses nucleic acids which differ from the nucleic acids shown in SEQ ID NO:1, but which have the same phenotype. Such nucleic acids are different with respect to their nucleotide sequence but are related and considered by those skilled in the art to be "functionally equivalent nucleic acids." Thus, the term "functionally equivalent" in reference to nucleic acid molecules encompasses nucleic acids having slight or non-consequential sequence variations so long as they function in substantially the same manner to produce substantially the same protein product(s) as the nucleic acids disclosed herein. In particular, for example, functionally equivalent nucleic acid molecules encode polypeptides that are the same as those encoded by the nucleic acids disclosed herein, or nucleic acids that encode, for example, conservative amino acid substitutions. Conservative substitutions include, for example, replacement of a nonpolar residue with another nonpolar residue, or replacement of a charged residue with a charged residue. Functionally equivalent nucleic acids also include minor modifications recognized by skilled artisans as those that do not substantially alter the tertiary structure of an encoded protein, such as internal deletions or truncations that produce, for example, minor deletions at the carboxy and amino termini.

Further provided are nucleic acids encoding A2BP polypeptides that, by virtue of the degeneracy of the genetic code, do not necessarily hybridize to the invention nucleic acids. Nevertheless, such nucleic acids are functionally equivalent because they can produce substantially the same protein product(s). Preferred nucleic acids encoding invention A2BPs are comprised of nucleotides that encode substantially the same amino acid sequence as set forth in SEQ ID NO:1.

Thus, an exemplary nucleic acid encoding an invention A2BP may be selected from:
(a) DNA encoding the amino acid sequence set forth in SEQ ID NO:2,
(b) DNA that hybridizes to the DNA of (a) under moderately stringent conditions, wherein said DNA encodes biologically active A2BP, or
(c) DNA degenerate with respect to either (a) or (b) above, wherein said DNA encodes biologically active A2BP.

Hybridization refers to the binding of nucleic acid molecules that exhibit complementarity to each other through hydrogen bonds, similar to the bonds that naturally occur in chromosomal DNA (i.e., sense:antisense strands or probe::target DNA). Stringency levels used to hybridize a given nucleic acid probe with target DNA such that the hybrid is stable can readily be determined and, if desired, varied by those of skill in the art.

As used herein, the term "stringent hybridization" refers to conditions under which polynucleic acid hybrids are stable. As known to those of skill in the art, the stability of hybrids is reflected in the melting temperature ($T_m$) of the hybrids, which is determined by the G:C content of the sequence, sequence length, and other physical characteristics and hybridization conditions known in the art (Sambrook et al., supra, 1989). For example, the amount of sodium ion present affects the stability of a hybrid. Typically, the hybridization or binding step is performed under conditions of lower stringency, followed by washes of varying, but higher, stringency. Reference to the level of hybridization stringency relates to such washing conditions.

The phrase "moderately stringent hybridization" refers to conditions that permit target DNA to bind a complementary nucleic acid that has about 60% identity, preferably about 75% identity, more preferably about 85% identity to the target DNA; with greater than about 90% identity to target DNA being especially preferred. Preferably, moderately stringent conditions are conditions equivalent to hybridization, for example, in 50% formamide, 5×Denhardt's solution, 5×SSPE, 0.2% SDS at 420° C., followed by washing in 0.2×SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhardt's solution, 6×SSPE, 0.2% SDS at 42° C., followed by washing in 1×SSPE, 0.2% SDS, at 50° C. Denhardt's solution and SSPE are well known to those of skill in the art as are other suitable hybridization and wash buffers (Sambrook et al., supra, 1989).

As used herein, the term "degenerate" refers to triplet codons that differ in at least one nucleotide from a reference nucleic acid, but encode the same amino acid as the reference nucleic acid. For example, codons specified by the triplets "UCU", "UCC", "UCA", and "UCG" are degenerate with respect to each other since all four of these codons encode the amino acid serine. Nucleic acids degenerate with respect to invention nucleic acids are explicitly contemplated in the invention.

Preferred nucleic acids encoding invention polypeptide(s) hybridize under moderately stringent, preferably high stringency conditions to substantially the entire sequence, or substantial portions (i.e., typically at least 15 nucleotides) of the nucleic acid sequence set forth nucleotides 987–1979 in SEQ ID NO:1.

The invention nucleic acids can be produced by a variety of methods well-known in the art, for example, using the methods described herein such as PCR amplification employing oligonucleotide primers from various regions of SEQ ID NO:1, and the like. Invention nucleic acids can be synthetically produced by commercial vendors, such nucleic acids additionally being modified or substituted with nucleotide analogs.

In accordance with a further embodiment of the invention, optionally labeled A2BP-encoding cDNAs, or fragments thereof, can be employed as probes to screen library(ies), such as cDNA, genomic, EST, and the like, for additional nucleic acid sequences encoding novel mammalian A2BPs. Such libraries are commercially available or can be constructed using methods well known in the art. Screening of a library with a DNA probe is initially carried out under low stringency conditions, which comprise a temperature of less than about 42° C., a formamide concentration of less than about 50%, and a moderate to low salt concentration.

Presently preferred nucleic acid hybridization screening conditions comprise a temperature of about 37° C., a formamide concentration of about 20%, and a salt concentration of about 5×standard saline citrate (SSC; 20×SSC contains 3M sodium chloride, 0.3M sodium citrate, pH 7.0). Such conditions allow the identification of sequences having a substantial degree of similarity with a DNA probe sequence, without requiring perfect homology. The term "substantial similarity" refers to nucleotide sequences which share at least about 50% homology. Preferably, hybridization conditions will be selected which allow the identification of sequences having at least about 70% homology with the probe, while discriminating against sequences which have lesser homology to the probe. As a result, nucleic acids having substantially the same nucleotide sequence as SEQ ID NO:1 can be obtained.

As used herein, the term "probe" refers to a molecule such as a nucleic acid (e.g., DNA) or protein (e.g., antibody) that can be used to identify, isolate, or quantify a gene, gene product or protein. For example, a nucleic acid probe generally is single stranded DNA or RNA, or analog thereof, having a sequence of nucleotides of at least 14, at least 20, at least 50, at least 100, at least 200, at least 300, at least 400, or at least 500 contiguous bases that are the same as (or the complement of) any contiguous bases set forth in SEQ ID NO:1. Preferred regions from which to construct such a DNA probe include 5' or 3' coding regions of SEQ ID NO:1. If desired, the entire CDNA encoding region of an invention A2BP, or the entire sequence corresponding to SEQ ID NO:1, can be used as a probe. Probes can be labeled by methods well known in the art, as described below, and can be used in various commercially available diagnostic kits, as described hereinafter.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in Gconjunction with additional reagents. In one embodiment, the indicating group is an enzyme, such as horseradish peroxidase (HRP), glucose oxidase, and the like. In another embodiment, radioactive elements, such as $^{32}$P, $^{33}$P $^{35}$S, $^{125}$I, and the like, are employed as labels. Additional types of labels are well known in experimental and clinical diagnostic chemistry.

The labeling means can be a fluorescent labeling agent which chemically binds to antibodies or antigens without denaturation to form a fluorochrome (dye) and can be useful to produce an immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

The linking of a label to a substrate, such as nucleic acids, antibodies, polypeptides, and proteins, is well known in the art. For instance, an invention antibody can be directly labeled by iodination or labeled by metabolic incorporation of radiolabeled amino acids provided in the culture medium (see, for example, Galfre et al., *Meth. Enzymol.* 73:3–46 (1981)). Conventional means of protein conjugation or coupling by activated functional groups are particularly applicable (see, for example, Aurameas et al., *Scand. J. Immunol.* Vol. 8, Suppl. 7:7–23 (1978); Rodwell et al., *Biotech.* 3:889–894 (1984) and U.S. Pat. No. 4,493,795).

In accordance with another embodiment of the present invention, there are provided isolated mammalian ataxin-2 binding proteins (A2BPs), and functional fragments thereof. The term "A2BP" refers to substantially pure native A2BP and naturally occurring allelic variants thereof, or recombinantly produced proteins, such as those produced by invention nucleic acids. A2BP also includes fragments thereof that retain at least one native biological activity, such as the ability to bind to a ataxin-2, the ability to bind nucleic acid, or having immunogenicity. Invention A2BPs additionally include A2BPs and functional fragments thereof contained within a larger amino acid sequence.

In one embodiment, invention A2BPs are characterized by having the ability to bind to at least one form of ataxin-2 protein encoded by a SCA2 gene. In another embodiment, A2BPs referred to herein are those polypeptides specifically recognized by an antibody that also specifically recognizes a A2BP (preferably human) including an amino acid sequence set forth in SEQ ID NO:2. Invention isolated A2BPs are free of cellular components or contaminants normally associated with a native in vivo environment.

The invention proteins are further characterized by being ubiquitously expressed, including expression in mammalian brain. Splice variant cDNA transcripts generated by alternative splicing of a primary transcript and allelic variants encoding A2BP family of proteins also are contemplated by the present invention.

Presently preferred A2BPs of the invention include amino acid sequences that comprise substantially the same sequence as the protein sequence set forth in SEQ ID NO:2, as well as biologically active, modified forms thereof. As discussed above, each of the invention A2BP proteins bind to ataxin-2, ataxin-2 like proteins or to nucleic acid. The A2BP set forth in SEQ ID NO:2 was identified in a screen of binding proteins using ataxin-2, and are contemplated as being involved in the signal transduction pathway affecting cell survival. In addition, the invention A2BP protein corresponding to SEQ ID NO:2 has highly conserved RNA binding motifs corresponding to amino acid sequences 119–124 and 156–162 of SEQ ID NO:2 (referred to as RNP-1 and RNP-2,respectively), and, therefore, similarly are contemplated herein as having a role in the signal transduction pathway affecting cell survival.

Those of skill in the art will recognize that numerous residues of the above described invention proteins can be substituted with other, chemically, sterically and/or electronically similar residues without substantially altering the biological activity of the resulting species. In addition, larger polypeptide sequences containing substantially the same sequence as set forth in SEQ ID NO:2 therein (e.g., splice variants and allelic polymorphisms) are contemplated.

As used herein, the term "substantially the same amino acid sequence" refers to amino acid sequences having at least about 70% identity with respect to the reference amino acid sequence which retains comparable functional and biological activity characteristic of the protein defined by the reference amino acid sequence. Preferably, proteins having substantially the same amino acid sequence will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice or allelic variants or that are modified by minor deletions, by conservative amino acid substitutions, by substitution of degenerate codons, or the like, also are encompassed within the scope of the present invention.

The term "biologically active" or "functional", when used herein as a modifier of invention A2BP(s), or polypeptide fragment thereof, refers to a polypeptide that exhibits one or more characteristics similar to A2BP. For example, biologically active A2BP can have the ability to bind, preferably in vivo, to at least one form of ataxin-2 encoded by a SCA2 gene. Ataxin-2 binding activity can be assayed, for example, using methods described in Examples I, II and III. Biologically active A2BP also can have the ability to bind nucleic acid, such as RNA and, therefore, such an invention polypeptide has RNA binding capability. RNA binding A2BP fragments contain amino acid sequences set forth in SEQ ID NO:2. Nucleic acid binding by invention A2BPs, or fragments thereof, can be determined using methods, such as electrophoretic gel shift analysis, known in the art. Exemplary functional fragments that bind to a nucleic acid, such as RNA, comprise amino acids 119–124 and/or 156–162 of SEQ ID NO:2.

Also encompassed by the term A2BP are functional fragments or polypeptide analogs thereof. The term "functional fragment" refers to a peptide fragment that is a portion of a full length A2BP protein, provided that the portion is biologically active, as defined above (i.e., has a characteristic of the corresponding full length protein).

In one embodiment, a functional fragment of an invention A2BP protein, such as a region contained in SEQ ID NO:2, has ataxin-2 binding capability but lacks a signal transduction function. In another embodiment, a functional fragment of A2BP has RNA binding capability but lacks a signal transduction function. Such functional fragments that bind ataxin-2 or RNA but do not transduce a signal, such as a cell degeneration or survival signal, can be useful, for example, as a dominant-negative inhibitor. Such an inhibitor can inhibit, in vivo, the binding of native (i.e. endogenous) A2BP to ataxin-2, RNA, or the like and can be useful in a method of the invention. For example, a dominant negative inhibitor that inhibits the cell degeneration signal transduction pathway can be used to treat disorders characterized by cell degeneration, and the like.

Biologically active A2BP polypeptides, such as a dominant-negative fragment, can be identified using well-known methods, such as binding assays described herein. Such methods include, for example, yeast or mammalian two-hybrid assay systems, in vitro nucleic acid binding assays and other competition binding-inhibition assays known in the art. In particular, such two-hybrid assay systems can be used to identify A2BP functional fragments that inhibit the binding of a A2BP to a ataxin-2 in vivo.

Functional fragments of A2BP also can elicit an immune response which is useful for obtaining polyclonal and monoclonal antibodies that bind specifically to an invention A2BP. Thus, an invention nucleic acid encoding an A2BP will encode a polypeptide specifically recognized by an antibody that also specifically recognizes the A2BP protein (preferably human) including the amino acid set forth in SEQ ID NO:2. Such immunologic activity may be assayed by any method known to those of skill in the art. For example, a test polypeptide encoded by a A2BP cDNA can be used to produce antibodies, which are then assayed for their ability to bind to an invention A2BP protein including the sequence set forth in SEQ ID NO:2. If the antibody binds to the test polypeptide and the protein including the sequence encoded by SEQ ID NO:2 with substantially the same affinity, then the polypeptide is biologically active in that it possesses immunogenic activity.

The amino acid length of functional fragments or polypeptide analogs of the present invention can range from about 5 amino acids up to the full length protein sequence of an invention A2BP. In certain embodiments, the amino acid lengths include, for example, at least about 10 amino acids, at least about 20, at least about 30, at least about 40, at least about 50, at least about 75, at least about 100, at least about 150, at least about 200, at least about 250 or more amino acids in length up to the full length A2BP protein sequence. Exemplary functional fragments that bind to a nucleic acid, such as RNA, comprise amino acids 119–124 and/or 156–162 of SEQ ID No:2.

The invention A2BPs can be isolated by a variety of methods well-known in the art, such as recombinant expression systems described herein, precipitation, gel filtration, ion-exchange, reverse-phase and affinity chromatography, and the like. Other well known methods are described in Deutscher et al. (*Guide to Protein Purification: Methods in Enzymology* Vol. 182, Academic Press (1990), which is incorporated herein by reference). Alternatively, the isolated polypeptides of the present invention can be obtained using well known methods, such as expression screening, employing, for example, invention antibodies.

An example of a means for preparing the invention polypeptide(s) is to express nucleic acids encoding a A2BP in a suitable host cell, such as a bacterial cell, a yeast cell, an insect cell, an amphibian cell (i.e., oocyte), or a mammalian cell, using methods well known in the art, and recovering the expressed polypeptide, again using well known methods. Invention polypeptides can be isolated directly from cells that have been transformed with expression vectors as described below herein. The invention polypeptide, functional fragments, and functional equivalents thereof also can be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

The term "polypeptide analog" includes any polypeptide having an amino acid sequence substantially the same as a sequence specifically shown herein in which one or more residues have been conservatively substituted with a functionally similar residue and which displays the ability to functionally mimic an A2BP as described herein. Examples of conservative substitutions include the substitution of one nonpolar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

As used herein the term "conservative substitution" includes the use of a chemically derivatized residue in place of a non-derivatized residue, provided that a polypeptide containing such a residue displays the required binding activity. The term "chemical derivative" refers to a subject polypeptide having one or more chemically derivatized residues produced by reaction, for example, of a functional side chain. Such derivatized molecules include those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are peptides containing one or more naturally occurring amino acid derivatives of the twenty standard amino acids, such as 4-hydroxyproline substituted for proline; 5-hydroxylysine substituted for lysine; 3-methylhistidine substituted for histidine; homoserine substituted for serine; and ornithine substituted for lysine.

Polypeptides of the present invention include any polypeptide having one or more deleted residues, relative to the sequence of a polypeptide whose sequence is shown herein, so long as the required activity is maintained. Similarly, additions to invention polypeptides are contemplated so long as the required biological activity is maintained.

An example of an addition to invention polypeptide is a heterologous domain. As used herein, the term "heterologous domain" is used broadly to mean an entity that is covalently attached to an invention protein which imparts a distinct function upon it to form a chimera. As used herein, the term "chimera" means an invention A2BP or functional fragment thereof that is covalently attached to one or more heterologous domains.

A heterologous domain essentially can be any small molecule, macromolecule or microfabricated device so long as it imparts a distinct function upon the invention protein(s) without substantial impairment of biological function. Such heterologous domains include, for example, those that provide a targeting function, or enhance, suppress or modulate the activity of A2BP or are useful for purification or the bioassays disclosed herein (e.g., the yeast two-hybrid assay system). For example, ligands to cell surface proteins that facilitate cell entry, such as antibodies, viral envelope proteins, growth factors, fragments thereof, and the like can provide targeting. Regulatory domains, such as derepressible steroid hormone binding domains, and the like can be useful for modulating the activity of A2BP invention polypeptides. A heterologous domain that is an RNAse can target RNA molecules that bind A2BP for degradation. Tags, such as biotin, T7, polyhistidine, and the like can be useful for the detection of proteins or nucleic acids that bind invention polypeptides, or purification of linked invention protein can be useful for purification or diagnostic assays. Those skilled in the art readily can determine the nature of a heterologous domain depending on the application and the distinct function desired. Thus, the invention provides chimeras comprising A2BP or functional fragments thereof and one or more heterologous domains.

The present invention also provides compositions containing an acceptable carrier and any of an isolated, purified A2BP mature protein or functional polypeptide fragments thereof or chimeras, alone or in combination with each other. Such polypeptides or proteins can be recombinantly derived, chemically synthesized or purified from native sources. As used herein, the term "acceptable carrier" encompasses any of the standard pharmaceutical carriers suitable for therapeutic administration, such as phosphate buffered saline solution, water and emulsions such as an oil/water or water/oil emulsion, and various types of wetting agents. Such pharmaceutical carriers further encompass carriers capable of traversing the blood-brain barrier.

The A2BP compositions described herein can be useful, for example, in methods for modulating the expression or activity of ataxin-2 proteins, or other proteins involved in glutamine related disease signal transduction pathways (e.g., ataxin-1, Huntingtin, Machado-Joseph, and the like). As used herein the phrase "modulating the activity" or grammatical variations thereof, refers to either inhibition of activity (as with an antagonist) or the activation of activity (as with an agonist). For example, an ataxin-2 activity contemplated herein for modulation includes inhibiting or activating the signal transduction pathway associated with cell degeneration. Thus, in accordance with another embodiment of the invention, methods for modulating the activity of a protein that binds A2BP, preferably ataxin-2 protein, comprising contacting ataxin-2 with a substantially pure A2BP, or functional fragment thereof, are provided.

Also provided are antisense nucleic acids containing a sequence capable of binding specifically with full length or any portion of a nucleic acid that encodes A2BP polypeptides. Such an antisense composition can be useful, for example, to inhibit translation of an mRNA that encodes a A2BP. An antisense nucleic acid may have a sequence capable of binding specifically to any portion of the sequence of the CDNA encoding A2BP polypeptides. As used herein, the term "binding specifically" encompasses a nucleic acid sequence that recognizes a nucleic acid molecule exhibiting sequence complementarity which forms double-helical segments therewith via the formation of hydrogen bonds between complementary base pairs. An example of an antisense nucleic acid is an antisense nucleic acid comprising chemical analogs of nucleotides.

Compositions comprising an antisense nucleic acid, as described above, in an amount effective to reduce expression of a human A2BP polypeptide and an acceptable hydrophobic carrier capable of passing through a cell membrane by passing through a cell membrane and binding specifically to nucleic acid encoding an A2BP polypeptide also are provided herein. Suitable hydrophobic carriers are described, for example, in U.S. Pat. Nos. 5,334,761; 4,889,953; 4,897,355, and the like. The acceptable hydrophobic carrier capable of passing through cell membranes also can contain a receptor component or like structure which binds to cells to facilitate entry. For example, a receptor component or like structure in a lipid vesicle carrier can be specific for a selected cell type thereby targeting an antisense nucleic acid to a selected cell type. The structure may be part of a protein known to bind to a cell-type specific receptor.

Antisense nucleic acid compositions can be useful to inhibit translation of mRNA encoding invention polypeptides. Similarly, synthetic oligonucleotides, or other antisense chemical structures can be designed to bind to mRNA encoding A2BP polypeptides and inhibit translation of mRNA. Such compositions can be useful to inhibit expression of A2BP associated genes in a tissue sample or in a subject.

In accordance with another embodiment of the invention, there are provided kits for detecting mutations, duplications, deletions, rearrangements and aneuploidies in A2BP genes comprising at least one invention probe or antisense nucleotide.

The present invention provides compositions useful for modulating expression of A2BP polypeptide. For example, synthetic antisense nucleic acid compositions (hereinafter SANC) can be employed to inhibit translation of mRNA encoding invention polypeptides. Synthetic oligonucleotides, or other antisense nucleic acid chemical structures designed to recognize and selectively bind to mRNA, are constructed to be complementary to full length or portions of an A2BP coding strand, including nucleotide sequences set forth in SEQ ID NO:1. The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC which render it capable of passing through cell membranes, for example, by designing small, hydrophobic SANC chemical structures, or by virtue of specific transport systems in the cell which recognize and transport the SANC into the cell. In addition, the SANC can be designed for targeting certain selected cell populations, for example, by employing a SANC that is recognized by specific cellular uptake mechanisms within select cell populations. For example, the SANC can be designed to bind to a receptor found only in a certain cell type, as discussed supra. In a particular embodiment, the SANC is an antisense oligonucleotide.

The SANC also is designed to recognize and selectively bind to target mRNA sequence, which may correspond to a sequence contained within the sequences shown in SEQ ID NO:1. The SANC is designed to inactivate target mRNA sequence by either binding thereto and inducing degradation of the RNA by, for example, RNase I digestion, or inhibiting splicing of pre-mRNA, or inhibiting translation of the mRNA target by interfering with the binding of translation regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *Trends Pharmacol. Sci.* 10:435–437 (1989) and Weintraub, *Sci. American*, January (1990), pp.40; both of which are incorporated herein by reference).

In accordance with yet another embodiment of the present invention, methods are provided for recombinant production of invention A2BPs by expressing the above described nucleic acid sequences in suitable host cells. Recombinant DNA expression systems that are suitable to produce A2BPs described herein are well known in the art. For example, the above described nucleotide sequences can be incorporated into vectors for further manipulation, propagation and protein expression. As used herein, the term "vector" (or plasmid) refers to discrete elements that are used to introduce heterologous DNA into cells for a variety of purposes.

Suitable expression vectors are well known in the art, and include, for example, vectors capable of expressing DNA operatively linked to a regulatory sequence, such as a promoter region that is capable of directing expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that replicate to high or low copy numbers in eukaryotic cells or prokaryotic cells, those that remain episomal and those that can integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate transcription initiation, such as cis acting elements which may be responsive to trans acting factors. Promoters, depending upon the nature of the regulation, can be constitutive or regulated. Such regulated promoters can be inducible or repressible such that expression of the DNA can be enhanced or repressed. Exemplary promoters contemplated for use in the practice of the present invention include the SV40 early promoter, the cytomegalovirus (CMV) promoter, the steroid inducible mouse mammary tumor virus (MMTV) promoter, Moloney murine leukemia virus (MMLV) promoter, the tetracycline regulated expression system, and the like.

As used herein, the term "operatively linked" refers to the functional relationship of DNA with regulatory and effector nucleotide sequences, such as promoters, enhancers, transcriptional and translational start and stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to, and transcribes the DNA.

As used herein, the term "expression" refers to any number of steps comprising the process by which polynucleic acids are transcribed into RNA, and translated into peptides, polypeptides, or proteins. If the polynucleic acid is derived from genomic DNA, expression may, if an appropriate eukaryotic host cell or organism is selected, include splicing of the RNA. Likewise, expression is to include postranslational processing, such as proteolytic cleavage and glycosylation, of polypeptides.

Transformation vectors suitable for expression and propagation in prokaryotes are well known in the art and include pBluescript, phage Lambda ZAP vectors (Stratagene, La Jolla, Calif.), and the like. Other suitable vectors and promoters are disclosed in detail in U.S. Pat. No. 4,798,885, which is incorporated herein by reference in its entirety.

Vectors suitable for transformation of *E. coli* cells include the pET expression vectors, such as pET11a, which contains the T7 promoter, T7 terminator, an inducible *E. coli* lac operator, and a lac repressor gene and pET 12a–c, which contains the T7 promoter, T7 terminator, and an *E. coli* ompT secretion signal (see U.S. Pat. No. 4,952,496). Other suitable vectors include, for example, pIN-IIIompA2, which contains an lpp promoter, a lacUV5 promoter operator, an ompA secretion signal, and a lac repressor gene (see Duffaud et al., *Meth. Enzymol.* 153:492–507 (1987)).

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg, *Nature*277:108–114 (1979)) the Okayama-Berg cloning system (*Mol. Cell Biol.* 2:161–170 (1982)), and the expression cloning vector described by Genetics Institute (U.S. Pat. No. 4,912,040), are available which provide assurance of at least some expression of the protein of interest in the transformed eukaryotic cell line.

Particularly preferred base vectors which contain regulatory elements that can be linked to the invention A2BP-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVO (Clontech, Palo Alto, Calif.).

Thus, in accordance with another embodiment of the present invention, there are provided "recombinant cells" containing the nucleic acid molecules of the present invention. Methods of transforming suitable host cells, preferably bacterial cells, and more preferably *E. coli* cells, as well as methods applicable for culturing said cells containing a gene encoding a heterologous protein, are generally known in the art (see, for example, Sambrook et al., supra, 1989).

Exemplary methods of transformation include, for example, transformation employing plasmids, viral, or bacterial phage vectors, transfection, electroporation, lipofection, and the like. The heterologous DNA can optionally include sequences which allow for its extrachromosomal (e.g., episomal) maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *S. cerevisiae, C. tropicalis, H. polymorpha* and *P. pastoris*; see, for example, U.S. Pat. Nos. 4,882,279; 4,837,148; 4,929,555 and 4,855,231), mammalian cells (for example, HeLa, HEK293, MDCK, BHK, CHO and Ltk⁻cells), insect cells, and the like. Presently preferred host organisms are bacteria. The most preferred bacteria is *E. coil.*

In one embodiment, nucleic acids encoding the invention A2BPs can be delivered into mammalian cells, either in vivo or in vitro using suitable viral vectors well known in the art. Suitable retroviral vectors, designed specifically for "gene therapy" methods, are described, for example, in U.S. Pat. Nos. 5,624,820, 5,693,508 and 5,674,703 and WIPO publications WO 92/05266 and WO 92/14829, which provide a description of methods for efficiently introducing nucleic acids into human cells. In addition, where it is desirable to limit or reduce expression of the invention A2BP, in vivo, the introduction of an antisense strand of an invention nucleic acid is contemplated.

Viral based systems provide the advantage of being able to introduce relatively high levels of a heterologous nucleic acid into a variety of cells. Additionally, such viruses can introduce heterologous DNA into nondividing cells. Suitable viral vectors for introducing invention nucleic acid encoding an A2BP protein into mammalian cells (e.g., vascular tissue segments) are well known in the art. These viral vectors include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561, 063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like. Especially preferred viral vectors are the adenovirus and retroviral vectors.

In one embodiment of the present invention, adenovirus-transferrin/polylysine-DNA (TfAdpl-DNA) vector complexes (Wagner et al., *PNAS. USA* 89:6099–6103 (1992), Curiel et al., *Hum. Gene Ther.* 3:147–154 (1992) and Gao et al., *Hum. Gene Ther.* 4:14–24 (1993)) are employed to transduce mammalian cells with heterologous A2BP nucleic acid. Any of the plasmid expression vectors described herein may be employed in a TfAdpl-DNA complex.

As used herein, "retroviral vector" refers to the well known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, for example, U.S. Pat. No. 4,650,764).

Suitable retroviral vectors for use herein are described, for example, in U.S. Pat. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the MMTV vectors (U.S. Pat. No. 5,646,013), vectors described supra, and the like.

In accordance with yet another embodiment of the present invention, there are provided anti-A2BP antibodies having specific reactivity with an A2BP polypeptides of the present invention. Active fragments of antibodies, such as Fab fragments and the like, are encompassed within the definition of "antibody".

Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies also can be produced by methods well known in the art. Such antibodies also can be produced by hybridoma, chemical synthesis or recombinant methods described, for example, in Sambrook et al., supra, 1989, and Harlow and Lane, supra, 1988. Both anti-peptide and anti-fusion protein antibodies can be used. (see, for example, Bahouth et al., *Trends Pharmacol. Sci.* 12:338–343 (1991) and Ausubel et al., *Current Protocols in Molecular Biology*, John Wiley and Sons, NY (1989), which are incorporated herein by reference).

Antibody so produced can be used, inter alia, in diagnostic methods and systems to detect an amount of A2BP present in a mammalian, preferably human, body sample, such as tissue (e.g., brain) or biological fluid (e.g., cerebrospinal fluid). Such antibodies also can be used for the immunoaffinity or affinity chromatography purification of invention A2BP. In addition, methods are contemplated herein for detecting the presence of an invention A2BP protein in a sample such as within a cell, in a compartment of the body, or in a biological fluid. The method comprises contacting the sample with an antibody that specifically binds to A2BP polypeptides, under conditions permitting binding of the antibody to A2BP polypeptides, detecting the presence of the antibody bound to an A2BP polypeptide, and thereby detecting the presence of invention polypeptides in the sample. With respect to the detection of such polypeptides, the antibodies can be used for in vitro diagnostic or in vivo imaging methods.

Procedures useful for in vitro detection of A2BP polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable label can be directly or indirectly attached to the antibody. Useful labels include, for example, radionucleotides, enzymes, fluorogens, chromogens and chemiluminescent substances, as described supra.

Invention anti-A2BP antibodies are contemplated for use herein to modulate the activity of an A2BP polypeptide in living animals, such as humans, or in biological tissues or fluids therefrom. The term "modulate" refers to a compound's ability to enhance (e.g., via an agonist) or inhibit (e.g., via an antagonist) the biological activity of an invention A2BP protein, such as the ataxin-2 binding or RNA binding activity of an A2BP. Accordingly, compositions comprising a carrier and an amount of an antibody having specificity for A2BP polypeptides effective to inhibit naturally occurring ligands or A2BP binding proteins (e.g., ataxin-2, and the like) from binding to invention A2BP polypeptides are contemplated herein. For example, a monoclonal antibody directed to an epitope of an invention A2BP polypeptide including an amino acid sequence set forth in SEQ ID NO:2 can be useful for this purpose. Such anti-A2BP antibodies additionally can be useful for inhibiting or enhancing the signal transduction pathway associated with cell degeneration.

The present invention further provides transgenic nonhuman mammals that are capable of expressing exogenous nucleic acids encoding A2BP polypeptides. As employed herein, the phrase "exogenous nucleic acid" refers to a nucleic acid sequence which is not native to the host, or which is present in the host in other than its native environment, for example, as part of a genetically engineered DNA construct that is introduced into the host. In addition to naturally occurring levels of A2BP, invention A2BPs can be overexpressed, such as in transgenic mammals.

Also provided are nonhuman transgenic mammals in which native A2BP is underexpressed, or not expressed at all (e.g., an A2BP knockout). In another embodiment, there are provided transgenic nonhuman mammals capable of expressing nucleic acids encoding A2BP polypeptides so mutated as to be incapable of native activity, i.e., do not express native A2BP.

Transgenic mammals in which a native A2BP gene locus has been knocked out, or replaced by a mutant A2BP gene to alter the expression or the structure of A2BP polypeptides expressed, can be produced by methods known in the art. Homologous recombination replaces a native (endogenous) gene with a mutated gene, recombinant gene, or unrelated gene, to produce an animal that cannot express native (endogenous) protein but can express, for example, a mutated protein which results in expression of altered A2BP polypeptides. The expression pattern of such a substituted gene can mimic that of the native (endogenous) gene which can be useful in determining, for example, the effect of A2BP mutations on various biological functions, such as developmental pathways. Homologous recombination techniques are well known in the art (see, for example, U.S. Pat. Nos. 5,721,367; 5,695,977; 5,650,298 and 5,614,396).

In yet another embodiment, the invention provides non-human transgenic mammals having a genome comprising antisense nucleic acids complementary to nucleic acids encoding A2BP polypeptides, placed so as to be transcribed into antisense mRNA complementary to mRNA encoding A2BP polypeptides, which hybridizes to the mRNA and, thereby, inhibits the translation thereof. The nucleic acid may additionally comprise a regulatable promoter or tissue specific regulatory elements, so that expression can be induced, repressed, or restricted to specific cell types. Examples of nucleic acids are DNA or cDNA having a coding sequence substantially the same as the coding sequence shown in SEQ ID NO:1. An example of a non-human transgenic mammal is a transgenic mouse. Examples of tissue specificity-determining expression elements are the metallothionein promoter and the L7 promoter. Protocols for producing transgenic mammals that express antisense nucleic acids capable of inhibiting translation of a sense nucleic acid are known in the art (U.S. Pat. No. 5,661,016).

Animal model systems which elucidate the biological roles of A2BP polypeptides also are provided, and are produced by creating transgenic animals as described above, for example, in which the expression of A2BP polypeptide is altered using a variety of techniques. Techniques for the insertion of normal or mutant versions of nucleic acids encoding an A2BP polypeptide include microinjection, retroviral infection or other means well known to those skilled in the art, into appropriate fertilized embryos to produce a transgenic animal (see, for example, Hogan et al., *Manipulating the Mouse Embryo: A Laboratory Manual* Cold Spring Harbor Laboratory (1986)).

In contrast to homologous recombination, microinjection can add genes to the host genome without removing a native A2BP gene. Thus, microinjection can produce a transgenic animal that is capable of expressing both endogenous (native) and exogenous A2BP. Regulatable promoters can be linked to the coding region of nucleic acids to provide a means to induce or repress expression of the transgene. If desired, tissue specific regulatory elements can be linked to the coding region to permit tissue-specific expression of the transgene. Transgenic animal model systems additionally are useful for in vivo screening of compounds for identification of specific ligands, such as agonists and antagonists, which activate or inhibit protein responses.

In addition to in vivo screening, invention nucleic acids (including antisense), oligonucleotides, vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of polypeptides, peptides or proteins.

Ataxin-2 is associated with development of spinocerebellar ataxia type-2; mutation of ataxin-2 by expansion of a polyglutamine repeat sequence results in the development of a neurodegenerative phenotype. Thus, ataxin-2 like other glutamine repeat genes (e.g., Machado-Joseph disease gene, Huntington disease gene, and the like) is thought to have a function in the signal transduction pathway that regulates cell degeneration. The binding of A2BP with ataxin-2 indicates that A2BP is a component of this signal transduction pathway and, therefore, the regulation of cell degeneration. In addition, through the identification of the invention binding proteins of ataxin-2, it has been discovered that ataxin-2 appears to have a role in gene regulation. For example, invention A2BPs comprising SEQ ID No:2 bind RNA thereby targeting RNA for degradation, or for the regulation of translation or splicing.

The functional characteristics of the invention A2BPs support the role of both ataxin-2 and the invention A2BPs in signal transduction pathways that effect cell degeneration. Ataxin-2 and invention A2BPs therefore also provide targets for treating a variety of pathologies, in which it is desired to increase or decrease cell degeneration. For example, invention A2BPs, agonist or antagonists thereto, can be used to treat neurodegenerative disorders, such as spinocerebellar ataxia type-2 and the like. In certain aspects of the invention, such as abnormal or undesirable cell proliferation, invention A2BPS, agonists or antagonists thereto can be used to treat disorders such as cancer.

Thus, in accordance with another embodiment of the present invention, there are provided methods for identifying compounds which bind to A2BP polypeptides. The invention proteins may be employed in a competitive binding assay. Such an assay can accommodate the rapid screening of a large number of compounds to determine which compounds, if any, are capable of binding to A2BPs. Subsequently, more detailed assays can be carried out with those compounds found to bind, to further determine whether such compounds act as modulators, agonists or antagonists of invention A2BP proteins. Such screening assays can be used to identify compounds having therapeutic value, for example, compounds that bind to or modulate invention A2BPs can be used to treat a variety of pathologies mediated by invention A2BPs. Such pathologies include those wherein cell degeneration is to be effected, for example, the previously described degenerative and hyperproliferative disorders.

In another embodiment of the invention, there are provided bioassays for identifying compounds which modulate the biological activity of invention A2BP polypeptides. According to this method, invention polypeptides are contacted with a "test" substance, the activity of the polypeptide is monitored subsequent to the contact with the test substance, and those substances which cause an effect on A2BP biological activity are identified as ligands for A2BP polypeptides. For example, a reporter gene expression system which monitors protein activity, such as a yeast or mammalian two-hybrid system that detects specific protein-protein interactions, can be used to screen compounds for agonist or antagonist activity. As exemplified in Examples I, II and III, a yeast two-hybrid system was used to detect protein-protein interactions between ataxin-2 and A2BP. Thus, compounds that enhance (agonists) or inhibit (antagonists) such protein-protein interactions, for example, between ataxin-2 and A2BP polypeptides, can be identified by contacting such yeast cells expressing recombinant proteins with a test compound. Antagonists will be identified as those compounds that inhibit protein-protein interactions thereby decreasing reporter expression whereas agonists will be identified as those compounds that enhance protein-protein interactions thereby increasing reporter expression.

Thus, the invention provides transformed host cells that recombinantly express invention polypeptides. The recombinant host cells can be contacted with a test compound, and the modulating effect(s) thereof can then be evaluated by comparing the A2BP mediated response (e.g., via reporter gene expression) in the presence and absence of test compound, or by comparing the response of test cells or control cells (i.e., cells that do not express A2BP polypeptides), to the presence of the compound.

Similarly, A2BP polypeptide binding to nucleic acids can be measured using a bioassay which detects nucleic acid (i.e. RNA or DNA) binding in vivo and in vitro. Thus, such an assay can be used to screen compounds for agonist and antagonist activity. Such nucleic acid binding assays, for example, in vitro electrophoretic gel shift assays, and the like, can be used to identify compounds that enhance or inhibit protein-nucleic acid binding.

As used herein, a compound or a signal that "modulates the activity" of invention polypeptides refers to a compound or a signal that alters the activity of A2BP polypeptides so that the activity of the invention polypeptide is different in the presence of the compound or signal than in the absence of the compound or signal. In particular, such compounds or signals include agonists and antagonists. An agonist encompasses a compound or a signal that activates A2BP. In contrast, an antagonist includes a compound or signal that inhibits A2BP. The effect of agonists and antagonists upon A2BP polypeptides can be direct or indirect. For example, an indirectly acting agonist may activate an intermediary, such as a protein, that in turn activates A2BP. Directly acting antagonists can be competitive, which interact with at or near the site specific for agonist binding, or noncompetitive, which interact with a site other than the agonist interaction site.

An example of such an antagonist is an A2BP that binds ataxin-2, but does not transduce a signal associated with cell degeneration. Likewise, an RNA binding A2BP which lacks a signal transducing capability associated with cell degeneration is an example of an antagonist.

As understood by those of skill in the art, methods for identifying compounds that modulate A2BP activity generally require comparison to a control. One type of a "control" is a cell or culture that is treated substantially the same as the cell or culture exposed to the test compound, with the distinction that the control cell or culture is not exposed to the test compound. For example, in methods that use voltage clamp electrophysiological procedures, the same cell can be tested in the presence or absence of compound, by merely changing the external solution bathing the cell. Another type of control cell or culture may be a cell or culture that is identical to the transfected cells, with the exception that the control cell or culture do not express native proteins. Accordingly, the response of the transfected cell to a test compound is compared to the response or lack thereof of the control cell or culture to the same compound under the same reaction conditions.

In another embodiment of the present invention, the activity of A2BP polypeptides can be modulated by contacting the polypeptides with an effective amount of at least one compound identified by the above described bioassays. In yet another embodiment, the activity of a protein that binds A2BP can be modulated by contacting such a protein with the invention polypeptides disclosed herein. The protein activity modulated can be enhanced or inhibited. For a protein that binds A2BP, such as ataxin-2, such a method can be useful for treating a pathology related to ataxin-2. Similarly, for a nucleic acid that binds A2BP or functional fragment thereof, the activity of said nucleic acid molecule can be modulated by employing the compositions of the invention.

In yet another embodiment, there are provided methods of treating degenerative or hyperproliferative disorders. The method comprises administering A2BP or functional fragment thereof to a subject. The invention also provides methods of treating disorders comprising administering nucleic acids encoding such A2BP polypeptides. Further provided are methods of treating disorders including those affecting the brain, such as spinocerebellar ataxia type-2. Methods of treating hyperproliferative disorders such as cancers also are provided.

Degenerative and hyperproliferative disorders can be treated by administering a A2BP or a functional fragment thereof. In regard to degenerative disorders, for example, the methods employ A2BP proteins wherein the polypeptides inhibit signal transduction which results in cell degeneration. For example, an A2BP polypeptide, such as a dominant-negative fragment (lacking a signal transducing function) that binds to ataxin-2 to inhibit ataxin-2's interaction with native (i.e. endogenous) A2BP, can be administered to a subject afflicted with spinocerebellar ataxia type-2 thereby alleviating symptoms associated with the disorder. In another embodiment, an RNA binding dominant-negative A2BP polypeptide (lacking a signal transducing function) similarly can be administered to a subject afflicted with spinocerebellar ataxia type-2 to inhibit transduction of the cell degeneration signal thereby alleviating associated symptoms. Such methods that employ dominant-negative A2BP polypeptides can inhibit a signal transduction pathway which results in cell degeneration associated with spinocerebellar ataxia type-2.

Nucleic acids encoding such therapeutic A2BP polypeptides and functional fragments thereof similarly can be employed in these methods. For example, administering a eukaryotic expression vector, such as a retroviral vector coding for a A2BP into a patient suffering a degenerative disorder, such as spinocerebellar ataxia type-2 can alleviate the symptoms associated with the disorder. Such vectors expressing therapeutic A2BP can, if desired, be targeted to the appropriate cell type using a retrovirus having a natural or engineered cell tropism. Preferred vectors for use in such methods are those capable of infecting cells that do not undergo cell division.

Additionally, a A2BP or functional fragment comprising a chimera, for example, a A2BP linked to a cell surface protein ligand (e.g, a nerve growth factor receptor or the like) can be administered to an individual to alleviate the symptoms associated with spinocerebellar ataxia type-2. Likewise, a chimera comprising A2BP linked to an RNAse can be administered to a subject to alleviate symptoms associated with spinocerebellar ataxia type-2. Similarly, such A2BP, functional fragments, and chimeras thereof encoded by nucleic acids can be administered to alleviate symptoms associated with degenerative disorders including, for example, spinocerebellar ataxia type-2.

Likewise, A2BP or ataxin-2 agonists and antagonists identified in the in vivo and in vitro assays described supra, as well as chimeras thereof and nucleic acids encoding same can be employed in a method of the invention to alleviate symptoms associated with degenerative disorders.

In another embodiment, the invention provides methods of treating hyperproliferative disorders such as cancer. The methods employ A2BP polypeptides wherein such polypeptides can stimulate a cell degeneration signal transduction pathway. Thus, using the modes of administration and expression systems (e.g., retroviral expression vectors and the like) invention polypeptides can be administered to subjects exhibiting abnormal or undesirable cellular proliferation to enhance cell degeneration thereby alleviating symptoms associated with hyperproliferation. Similarly, A2BP or ataxin-2 agonists or antagonists identified by the methods described supra can be employed in the methods to enhance cell degeneration.

The methods described above employ routes of administration well known to those skilled in the art. Such routes include, for example, intravenous, intramuscular, subcutaneous, intraspinal, and intracranial. The routes chosen will depend on the disorder to be treated and the compositions employed.

In accordance with another embodiment of the present invention, there are provided methods for diagnosing disorders related to A2BP, said method comprising: detecting, in said subject, a defective sequence, mutant of SEQ ID NO:1.

In accordance with another embodiment of the present invention, there are provided diagnostic systems, preferably in kit form, comprising at least one invention nucleic acid in a suitable packaging material. The diagnostic nucleic acids are derived from the A2BP-encoding nucleic acids described herein. In one embodiment, for example, the diagnostic nucleic acids are derived from SEQ ID NO:1. Invention diagnostic systems are useful for assaying for the presence or absence of nucleic acid encoding A2BP in either genomic DNA or in transcribed nucleic acid (such as mRNA or cDNA) encoding A2BP.

A suitable diagnostic system includes at least one invention nucleic acid, preferably two or more invention nucleic acids, as a separately packaged chemical reagent(s) in an amount sufficient for at least one assay. Instructions for use of the packaged reagent also are typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding A2BP including the nucleotide sequences set forth in SEQ ID NO:1 or mutations or deletions therein, thereby diagnosing the presence of, or a predisposition for, spinocerebellar ataxia type-2. In addition, the packaging material contains instructions indicating how the materials within the kit are employed both to detect a particular sequence and diagnose the presence of, or a predisposition for, spinocerebellar ataxia type-2, for example.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

Materials and Methods

Unless otherwise stated, the present invention was performed using standard procedures, as described, for example in Maniatis et al., *Molecular Cloning: A Laboratory Manual*, Cold Spring Harbor Laboratory Press, Cold Spring Harbor, New York, USA (1982); Sambrook et al., *Molecular Cloning: A Laboratory Manual* (2 ed.), Cold Spring Harbor Laboratory Press, Cold Spring Harbor, New York, USA (1989); Davis et al., *Basic Methods in Molecular Biology*, Elsevier Science Publishing, Inc., New York, USA (1986); or *Methods in Enzymology: Guide to Molecular Cloning Techniques* 152, S. L. Berger and A. R. Kimmerl Eds., Academic Press Inc., San Diego, USA (1987)).

EXAMPLE 1

Identification of cDNA Encoding Ataxin-2 Binding-Proteins

A plasmid that codes for the C-terminal region of ataxin-2 protein (amino acids 811–1312; see Pulst et al., 1996, *Nature Genetics*, 14:269–276) was fused to the binding domain of the transcription factor GAL4 to form the plasmid pSCA2U4L2. A human adult brain cDNA library was cloned into a GAL4 activation domain fusion vector pGAD10 (Clontech, Palo Alto, Calif.) and screened by the yeast two-hybrid method (Fields et al., *Nature* 340:245–246 (1989)), using the plasmid pSCA2U4L2. Yeast strain Y190 double-transformants were grown on SC media with leucine, tryptophane, and histidine dropped out, and with 25 mM 3-amino-1,2,4-triazole and 2% glucose (Poullet and Tamanoi, *Meth.in Enzym.*, 255:488–497 (1995)). β-galactosidase activity was assayed by incubating freeze-fractured colonies on nitrocellulose in Z-buffer (60 mM $Na_2HPO_4$, 40 mM $NaH_2PO_4$, 10 mM KCl, 1 mM $MgSO_4$, pH 7.0, 0.03 mM β-mercaptoethanol, and 2.5 μM X-gal) at 37° C. for 15 min to 8 hr.

A total of $2.2 \times 10^6$ colonies were screened, of which 15 were positive for β-galactosidase activity, evident by blue colonies. Plasmids were purified and cotransformed with pSCA2U4L2 which reduced the number of transformants producing blue colonies to 2. Both of the clones selected encoded a novel ataxin-2 binding protein set forth herein as (SEQ ID NO:1).

EXAMPLE 2

Characterization of Ataxin-2:Ataxin-2 Binding Protein Binding

To determine which domains of ataxin-2 bind to the ataxin-2-binding-protein, deletion constructs were generated containing amino and carboxy terminal deletions of ataxin-2 and tested using the above-described yeast two-hybrid method. Ataxin-2 proteins with carboxy-terminal residues deleted showed no interaction with ataxin-2 binding protein, whereas Ataxin-2 proteins with amino-terminal deletions of up to 1022 amino acids bound to the invention ataxin-2 binding protein. These results indicate that regions necessary for binding of invention A2BP to ataxin-2 are within amino acid residues 1023–1312 of ataxin-2.

Figure 2:
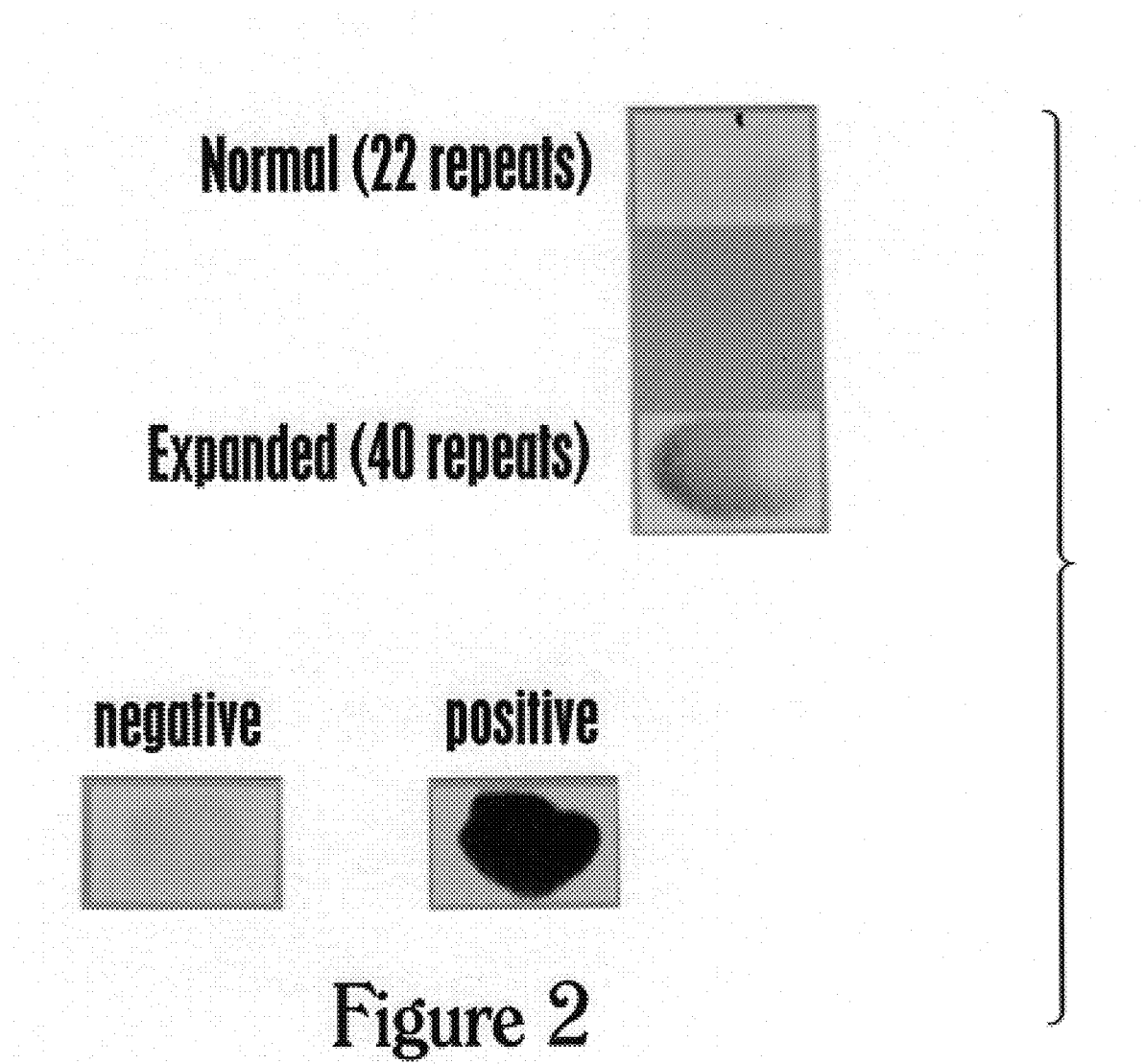
FIG. 2 shows the results of the polyglutamine expansion studies described in Example 2.

It has also been found that the polyglutamine (polyQ) repeat sequence in ataxin-2 is not essential for A2BP binding. However, as determined using a β-gal filter assay, binding affinity of A2BP for the full-length length pathogenic expanded ataxin-2 form containing 40 or polyglutamine residues, was greater than that for full-length normal ataxin-2 containing 22 poly-glutamine residues (see FIG. 2). The difference in binding affinities of ataxin-2 binding proteins for different CAG repeat lengths (polyglutamine repeats) indicates that the pathogenically expanded polyglutamine repeat of 40 and 58 glutamines enhances the binding interaction of A2BP for Ataxin-2 relative to a poly Q repeat of 22 glutamines.

Figure 3:
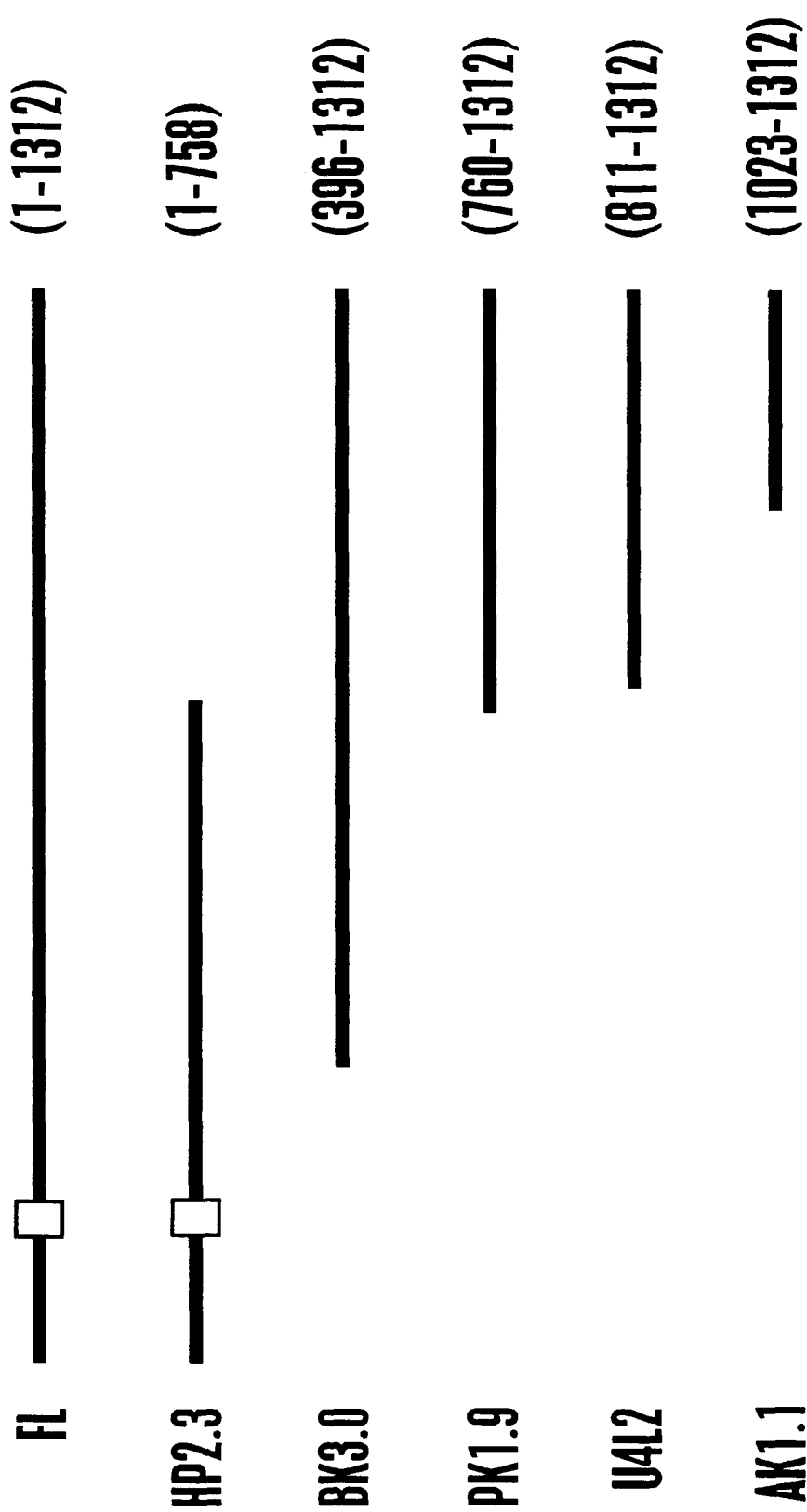
FIG. 3 shows a map of the Ataxin-2 deletion constructs described in Example 2.
Figure 4:
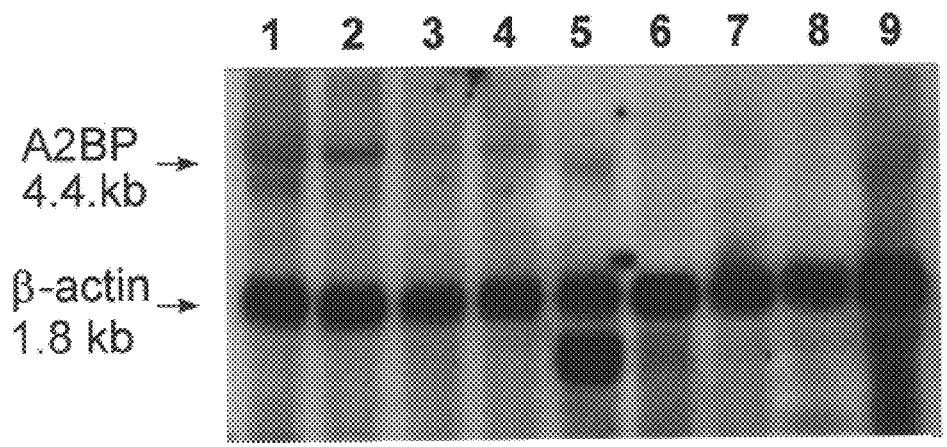
FIG. 4 shows the results of the Northern Blot assay described in Example 4.

The degree of interaction between ataxin-2 binding protein and ataxin-2 also was assessed using a semiquantitative ONPG liquid assay for β-galactosidase activity (Poullet and Tamanoi, supra (1995)). Several ataxin-2 deletion constructs were prepared and labeled "FL", "HP2.3", "BK3.0", "PK1.9", "UHL2" and "AK1.1". The corresponding amino acid regions of ataxin-2 for these E constructs are set forth in FIG. 3. The results indicate that β-galactosidase activities were higher for the ataxin-2 deletion construct U4L2 containing amino acids 811–1312 of ataxin-2 than for the PK1.9 deletion construct containing amino acids 760–1312 of ataxin-2 (see Table 1).

TABLE 1

Quantitative ONPG Liquid Assay

| AD constructs | BD constructs | β-gal activity |
| --- | --- | --- |
| A2BP1 | SCA2 FL | 0.9927 ± 0.1495 |
| A2BP1 | SCA2 PK1.9 | 100.8 ± 7.909 |
| A2BP1 | SCA2 U4L2 | 236.1 ± 18.69 |
| NF2B Cln5 | NF212 | 55.32 ± 11.07 |

Among the deletion constructs, only those expressing ataxin-2 carboxy terminal domains exhibited β-galactosidase activity. The full-length constructs presented low levels of β-galactosidase activity. This can be attributed to spatial limitations of the Gal4 assay system.

The results showing the interaction of ataxin-2 binding proteins with ataxin-2 are consistent with the observation that the SCA1 gene product ataxin-1, which is associated with spinocerebellar ataxia type-1, interacts with LANP, a leucine rich acidic nuclear protein. LANP and ataxin-1 colocalize in matrix-associated subnuclear structures (Matilla et al., Nature 389:974–978 (1997). Similar to the increased association of ataxin-2 binding protein with ataxin-2 having increased glutamine residues, the association of LANP with ataxin-1 is stronger when increasing the number of glutamine residues.

EXAMPLE 3

Immunohistochemical Staining Assay

To determine the distribution of ataxin-2 binding protein in the target tissues involved in the ataxia phenotype, antibodies to ataxin-2 binding protein and ataxin-2 were used to demonstrate that these proteins were present in the same cells, and that ataxin-2 binding protein was a target for ataxin-2 binding in vivo. Immunohistochemical staining was accomplished with 20 µg/ml of rabbit anti-ataxin-2 binding protein antibody, 20 µg/ml of rabbit preimmune serum incubated with tissue sections overnight at 4° C. Primary antibodies were detected using the Vector ABC elite Peroxidase Kit (Vector Labs, Burlingame, Calif.), DAB enhanced, and visualized with diaminobenzidine (DAB; Biomeda). Sections were counterstained using aqueous hematoxylin (Xymed). Absorption controls were conducted using the same antibody preabsorbed with peptide antigen at 100 µM for 3 hr at room temperature.

In the cerebellum (one of the tissues involved in spinocerebellar ataxia type-2), ataxin-2 and ataxin-2 binding protein expression were restricted to specific cell types. Both proteins were detected in Purkinje and dentate neurons, but little expression was seen in granule neurons. Staining of both proteins also was seen in selected neurons in the hypocampus, cerebral cortex, thalamus, and brain stem.

The ataxin-2 binding protein gene is abundantly expressed in Purkinje and dentate neurons and ataxin-2 binding protein has a distinct localization to the cytoplasm. Studies to determine whether ataxin-2 was localized to the same structures as ataxin-2 binding protein were performed. Adjacent sections of cerebellum were prepared and adjacent sections were stained with ataxin-2 binding protein and ataxin-2 antibodies. Clear colocalization of ataxin-2 binding protein and ataxin-2 with punctated organelles in the Purkinje and dentate neurons was observed.

The tissue distribution of ataxin-2 binding protein and ataxin-2 indicates that their interaction may be significant not only for such as spinocerebellar ataxia type-2, but also may explain neurodegenerative disorders involving other gene sequences which undergo glutamine repeat expansion. This interaction may point to common biological pathways for the group of clinically similar neurodegenerative disorders including spinocerebellar ataxia types 1 and 6, spinobulbar muscular atrophy, Huntington's disease and Machado-Joseph disease.

EXAMPLE 4

Northern Blot Analysis

Total RNA samples were extracted from different regions of mouse brain and rat cerebellum using Trizol reagent (GibcoBRL). The RNA was run on 1.2% agarose gel and blotted on GeneScreen Plus membrane using well-known methods (Du Pont). The fragment of A2BP (1/3 kb) was purified by Bgl II digestion of pGAD-A2BP, and was labeled with T4 kinase and $\gamma$-$^{32}$P-ATP. An equal amount of total RNA on each lane was confirmed by hybridization with β-actin as a control (Clontech).

The results indicate the presence of a 4.4 kb mRNA transcript encoding A2BP in the following mouse brain tissues: cerebellum (lane 1), cortex (lane 2), brain stem (lane 3), thalamus and hypothalamus (lane 4), and rat cerebellum (lane 9). A slightly smaller band was observed in heart (lane 5), indicating a potential splice-variant nucleic acid transcript.

EXAMPLE 5

Co-immunoprecipitation Assay

To demonstrate that A2BP binds to ataxin-2 in human cells, co-immunoprecipitation was performed in HTB10 Cells.

Rabbit anti-ataxin-2 antibodies, designated anti-SCA2A and anti-SCA2B antibodies, were raised against the peptides corresponding to amino acids 359–371 and amino acids 904–921, respectively, of the human ataxin-2 protein, which human ataxin-2 protein sequence is set forth in Pulst et al., 1996, *Nature Genetics*, 14:269–276. In addition, anti-A2BP antibodies, designated 1734–2, were raised against the peptide corresponding to amino acids 177–190 of the invention human A2BP. The primary antibodies were detected by ECL Western blotting detection system (available from Amersham).

Native HTB10 cells were harvested after 48 hrs incubation at 37° C. and homogenized in RIPA buffer (50 mM Tris-Cl, 0.1 % SDS, 0.5% deoxycholic acid, 1% Tween 20, 0.05% NaN$_2$) containing 2 μg/ml aprotinin, 1 μg/ml leupeptin, 500 μg/ml Pefabloc SC, 1 μg/ml pepstatin. The lysates were precleared for 1 hr each with formalin-fixed *Staphylocuccus aureus cells* (Sigma) and then with rabbit-serum agarose (Sigma) at room temperature. The precleared lysate was incubated with the anti-SCA2A antibody or with the anti-A2BP antibody "1734–2" at 4° C. overnight. Thereafter, Protein A/G resin (CytoSignal) was added to the lysate and incubated at 4° C. for 1 hr to recover the antigen-antibody complex. The resin was washed several times with RIPA buffer. The precipitated proteins were recovered from the resin through a spin filter column (CytoSignal) by centrifugation with 2×sample buffer (62.5 mM Tris, pH 6.8, 4% SDS, 20% glycerol, 5% β-mercaptoethanol, 0.0025% bromophenol blue). The endogenous expression of ataxin-2 and invention A2BP in HTB cells was confirmed with the anti-SCA2A antibody, the anti-SCA2B antibody and with anti-A2BP antibody 1734–2.

Figure 5:
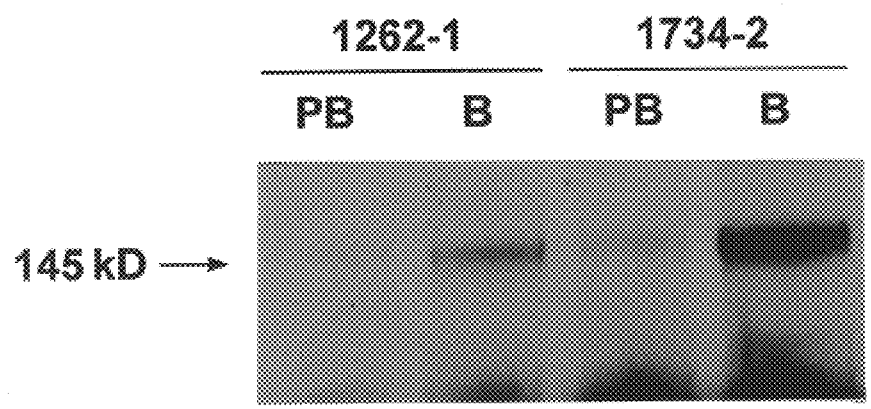
FIG. 5 shows the results of the co-immunoprecipitation assay described in Example 5.

As set forth above, the precleared lysate from the HTB10 cells was immunoprecipitated with either the anti-SCA2A antibody or the anti-A2BP antibody 1734–2. The precipitate was analyzed by Western blotting with anti-SCA2B antibody (FIG. 5). A single band of 145 kD which matched the expected size of endogenous ataxin-2, was detected on the sample precipitated with anti-A2BP antibody 1734–2 as well as with anti-SCA2A antibody (lanes B). No band was detected in the sample precipitated with the preimmune serum (lanes PB).

While the invention has been described in detail with reference to certain preferred embodiments thereof, it will be understood that modifications and variations are within the spirit and scope of that which is described and claimed.

What is claimed is:

1. An isolated nucleic acid encoding a functional fragment of A2BP referenced as SEQ ID NO:2, said functional fragment having ataxin-2 binding activity, nucleic acid molecule binding activity, or A2BP antigenic activity.

2. A nucleic acid according to claim 1, wherein said nucleic acid encodes amino acids 119 to 124 or 156 to 162 of SEQ ID NO:2.

3. An isolated nucleic acid according to claim 1, wherein said functional fragment binds ataxin-2.

4. An isolated nucleic acid according to claim 1, wherein said functional fragment binds a nucleic acid molecule.

5. An isolated nucleic acid encoding ataxin-2 binding protein (A2BP), wherein said nucleic acid is selected from the group consisting of:
   (a) DNA encoding the amino acid sequence set forth in SEQ ID NO:2,
   (b) DNA that hybridizes to the DNA of (a) under moderately stringent conditions, wherein said DNA that hybridizes encodes A2BP having an A2BP biological activity, and
   (c) DNA degenerate with respect to either (a) or (b) above, which DNA encodes A2BP having an A2BP biological activity.

6. A nucleic acid according to claim 5, wherein said nucleic acid hybridizes under high stringency conditions to the A2BP coding portion of SEQ ID NO:1.

7. A nucleic acid according to claim 5, wherein the nucleotide sequence of said nucleic acid is substantially the same as set forth as nucleotides 987–1979 of SEQ ID NO:1.

8. A nucleic acid according to claim 5, wherein the nucleotide sequence of said nucleic acid is the same as nucleotides 987–1979 of SEQ ID NO:1.

9. A nucleic acid according to claim 5, wherein said nucleic acid is cDNA.

10. A vector containing the nucleic acid of claim 1.

11. A recombinant cell containing the nucleic acid of claim 5.

12. A method for expression of A2BP or a functional fragment thereof, said method comprising culturing the cell of claim 11 under conditions suitable for expression of said A2BP.

13. A nucleic acid according to claim 5, wherein said nucleic acid is a DNA encoding the amino acid sequence set forth in SEQ ID NO:2.

14. A nucleic acid according to claim 5, wherein said nucleic acid is a DNA that hybridizes to the DNA of (a) under moderately stringent conditions and wherein said DNA that hybridizes encodes A2BP having an A2BP biological activity.

15. A nucleic acid according to claim 5, wherein said nucleic acid is a DNA degenerate with respect to either (a) or (b), which DNA encodes A2BP having an A2BP biological activity.

16. A nucleic acid according to claim 5, wherein said biological activity is ataxin-2 binding activity or nucleic acid molecule binding activity.

* * * * *

UNITED STATES PATENT AND TRADEMARK OFFICE
CERTIFICATE OF CORRECTION

PATENT NO. : 6,194,171 B1
DATED : February 27, 2001
INVENTOR(S) : Pulst, Stefan M., et al.

It is certified that error appears in the above-identified patent and that said Letters Patent is hereby corrected as shown below:

Column 32,
Line 19, please delete "of claim 1" and replace therefore with -- of claim 5 --.

Signed and Sealed this

Fourteenth Day of December, 2004

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 2372
<212> TYPE: DNA
<213> ORGANISM: Homo sapiens
<220> FEATURE:
<221> NAME/KEY: CDS
<222> LOCATION: (987)..(1979)

<400> SEQUENCE: 1
tccggctctc ctttgtttat tttctaatct atattttac tggaagattt cctctttatt      60
ctctcccgcc ctcctacaag cgctcttgct ggccgtctgg gtgcacacac cgctccctcg     120 atcacccag cccccttcct ggtctcccga gcgcggggtt tgaaggtcac ctcctttcca     180
gtccccgtgc gagccgcgct gccgccgcct cctccagcca gagtcggtgg gactggctgc     240
gctgccctga agtggttctc caagcagcgc ggagggtggc ggacggcgga cggagcccag     300
gggccgcgtc gggtggggaa acccgaactc gcggagggga atccctcccc cttcgcccca     360
gccccccagc agcaccgcg gtggggcggg ggcgctctgc cagcccggg aacagcagag      420 gcggcggcac tggctggacc cacgcgcgcg cctccggggc tgaagaagga aggagtgagc     480
cgagccgagc accccacatc tggaggggac agccagccgt gggcccgcc ccggcgtccg     540 gagcaggaga attccgagct tcttgcccag gcagagagag caggagcgga ccgcgcgccc    600
gggattgaga gtccttgcgc tccagacccc cacccagtgg ccgccaggtc ccgcctgtcc    660
ggaccctcgc cgcgcccagg caggcgcgcc agggcggggc tgacctgccc gcgaagttgc    720
ggacagtgcg tgagaaacca gcacccccct ccgccgcctc cagcttatgg tgagtgtggc    780
tgggggtgca gagagcgcac gggaattcgg gggtctgggg ccgagaacgt gaccgcagcc    840
gggctcgccg ggagttctag gaaactggtc aaagaactca tgcaagtgga acttacagct    900
tccttgatcg gactcagcat tcagatatca aagcagactg caataacctgc gtggaaatag   960 aagacagaaa ggtttcaaga caacag atg aat tgt gaa aga gag cag cta agg     1013
                          Met Asn Cys Glu Arg Glu Gln Leu Arg
```

-continued

|   | 1 |   |   |   | 5 |   |   |   |   |   |   |   |   |   |   |      |
|---|---|---|---|---|---|---|---|---|---|---|---|---|---|---|---|------|
| ggt | aat | cag | gaa | gca | gcc | gct | gcc | cct | gac | aca | atg | gct | cag | cct | tac | 1061 |
| Gly | Asn | Gln | Glu | Ala | Ala | Ala | Ala | Pro | Asp | Thr | Met | Ala | Gln | Pro | Tyr |      |
| 10 |   |   |   |   | 15 |   |   |   |   | 20 |   |   |   |   | 25 |      |

```
ggt aat cag gaa gca gcc gct gcc cct gac aca atg gct cag cct tac        1061
Gly Asn Gln Glu Ala Ala Ala Ala Pro Asp Thr Met Ala Gln Pro Tyr
 10              15                  20                  25 gct tcg gcc cag ttt gct ccc ccg cag aac ggt atc ccc gcg gaa tac        1109
Ala Ser Ala Gln Phe Ala Pro Pro Gln Asn Gly Ile Pro Ala Glu Tyr
                 30                  35                  40 acg gcc cct cat ccc cac ccc gcg cca gag tac aca ggc cag acc acg        1157
Thr Ala Pro His Pro His Pro Ala Pro Glu Tyr Thr Gly Gln Thr Thr
                 45                  50                  55 gtt ccc gag cac aca tta aac ctg tac cct ccc gcg cag acg cac tcc        1205
Val Pro Glu His Thr Leu Asn Leu Tyr Pro Pro Ala Gln Thr His Ser
                 60                  65                  70 gag cag agc ccg gcg gac acg agc gct cag acc gtc tct ggc acc gcc        1253
Glu Gln Ser Pro Ala Asp Thr Ser Ala Gln Thr Val Ser Gly Thr Ala
     75                  80                  85 aca cag aca gat gac gca gca ccg acg gat ggc cag ccc cag aca caa        1301
Thr Gln Thr Asp Asp Ala Ala Pro Thr Asp Gly Gln Pro Gln Thr Gln
 90              95                 100                 105 cct tct gaa aac acg gaa aac aag tct cag ccc aag cgg ctg cat gtc        1349
Pro Ser Glu Asn Thr Glu Asn Lys Ser Gln Pro Lys Arg Leu His Val
            110                 115                 120 tcc aat atc ccc ttc agg ttc cgg gat ccg gac ctc aga caa atg ttt        1397
Ser Asn Ile Pro Phe Arg Phe Arg Asp Pro Asp Leu Arg Gln Met Phe
            125                 130                 135 ggt caa ttt ggt aaa atc tta gat gtt gaa att att ttt aat gag cga        1445
Gly Gln Phe Gly Lys Ile Leu Asp Val Glu Ile Ile Phe Asn Glu Arg
            140                 145                 150 ggc tca aag gga ttt ggt ttc gta act ttc gaa aat agt gcc gat gcg        1493
Gly Ser Lys Gly Phe Gly Phe Val Thr Phe Glu Asn Ser Ala Asp Ala
155                 160                 165 gac agg gcg agg gag aaa tta cac ggc acc gtg gta gag ggc cgt aaa        1541
Asp Arg Ala Arg Glu Lys Leu His Gly Thr Val Val Glu Gly Arg Lys
170                 175                 180                 185 atc gag gta aat aat gcc aca gca cgt gta atg aca aat aaa aag acc        1589
Ile Glu Val Asn Asn Ala Thr Ala Arg Val Met Thr Asn Lys Lys Thr
                190                 195                 200 gtc aac cct tat aca aat ggc tgg aaa ttg aat cca gtt gtg ggt gca        1637
Val Asn Pro Tyr Thr Asn Gly Trp Lys Leu Asn Pro Val Val Gly Ala
                205                 210                 215 gtc tac agt ccc gaa ttc tat gca ggc acg gtc ctg ttg tgc cag gcc        1685
Val Tyr Ser Pro Glu Phe Tyr Ala Gly Thr Val Leu Leu Cys Gln Ala
                220                 225                 230 aac cag gag gga tct tcc atg tac agt gcc ccc agt tca ctt gta tat        1733
Asn Gln Glu Gly Ser Ser Met Tyr Ser Ala Pro Ser Ser Leu Val Tyr
235                 240                 245 act tct gca atg cca ggc ttc ccg tat cca gca gcc acc gcc gcg gcc        1781
Thr Ser Ala Met Pro Gly Phe Pro Tyr Pro Ala Ala Thr Ala Ala Ala
250                 255                 260                 265 gcc tac cga ggg gcg cac ctg cga ggc cgc ggt cgc acc gtg tac aac        1829
Ala Tyr Arg Gly Ala His Leu Arg Gly Arg Gly Arg Thr Val Tyr Asn
                270                 275                 280 acc ttc agg gcc gcg gcg ccc ccg ccc ccg atc ccg gcc tac ggc ggt        1877
Thr Phe Arg Ala Ala Ala Pro Pro Pro Pro Ile Pro Ala Tyr Gly Gly
                285                 290                 295 gtt gtt tac cca gga tgg att tta tgg tgc aga cat tta tgg tgg tta        1925
Val Val Tyr Pro Gly Trp Ile Leu Trp Cys Arg His Leu Trp Trp Leu
            300                 305                 310 tgc tgc ata ccg cta cgc cca gcc tac ccc tgc cac tgc cgc tgc cta        1973
```

```
Cys Cys Ile Pro Leu Arg Pro Ala Tyr Pro Cys His Cys Arg Cys Leu
    315                 320                 325 cag tga cagaaatcag ttcgtcttcg ttgcagcaga tgaaatttct tgtaacacct      2029
Gln
330
ctgcagttac ggacgagttt atgctgccga ccctaccac cacgcacttg ctccagcccc   2089
cacctacggc gttggtgcca tgaatgcttt tgcacctttg actgatgcca agactaggag   2149
ccatgctgat gatgtgggtc tcgttctttc ttcattgcag gctagtatat accgaggggg   2209
atacaaccgt tttgctccat actaaatgac aaaaccataa aaaccttcca atgtggggag   2269
aaaggaagct ttccgaggcc tgagtattgc aatacatgca gtagtacatc attttagcaa   2329
ttttaaaaaa aaaaaaaaat acaaaaaaaa aaaaaaaaa aaa                      2372

<210> SEQ ID NO 2
<211> LENGTH: 330
<212> TYPE: PRT
<213> ORGANISM: Homo sapiens

<400> SEQUENCE: 2

Met Asn Cys Glu Arg Glu Gln Leu Arg Gly Asn Gln Glu Ala Ala Ala
  1               5                  10                  15

Ala Pro Asp Thr Met Ala Gln Pro Tyr Ala Ser Ala Gln Phe Ala Pro
             20                  25                  30

Pro Gln Asn Gly Ile Pro Ala Glu Tyr Thr Ala Pro His Pro His Pro
         35                  40                  45

Ala Pro Glu Tyr Thr Gly Gln Thr Thr Val Pro Glu His Thr Leu Asn
     50                  55                  60

Leu Tyr Pro Pro Ala Gln Thr His Ser Glu Gln Ser Pro Ala Asp Thr
 65                  70                  75                  80

Ser Ala Gln Thr Val Ser Gly Thr Ala Thr Gln Thr Asp Asp Ala Ala
                 85                  90                  95

Pro Thr Asp Gly Gln Pro Gln Thr Gln Pro Ser Glu Asn Thr Glu Asn
            100                 105                 110

Lys Ser Gln Pro Lys Arg Leu His Val Ser Asn Ile Pro Phe Arg Phe
        115                 120                 125

Arg Asp Pro Asp Leu Arg Gln Met Phe Gly Gln Phe Gly Lys Ile Leu
    130                 135                 140

Asp Val Glu Ile Ile Phe Asn Glu Arg Gly Ser Lys Gly Phe Gly Phe
145                 150                 155                 160

Val Thr Phe Glu Asn Ser Ala Asp Ala Asp Arg Ala Arg Glu Lys Leu
                165                 170                 175

His Gly Thr Val Val Glu Gly Arg Lys Ile Glu Val Asn Asn Ala Thr
            180                 185                 190

Ala Arg Val Met Thr Asn Lys Lys Thr Val Asn Pro Tyr Thr Asn Gly
        195                 200                 205

Trp Lys Leu Asn Pro Val Val Gly Ala Val Tyr Ser Pro Glu Phe Tyr
    210                 215                 220

Ala Gly Thr Val Leu Leu Cys Gln Ala Asn Gln Glu Gly Ser Ser Met
225                 230                 235                 240

Tyr Ser Ala Pro Ser Ser Leu Val Tyr Thr Ser Ala Met Pro Gly Phe
                245                 250                 255

Pro Tyr Pro Ala Ala Thr Ala Ala Ala Tyr Arg Gly Ala His Leu
            260                 265                 270

Arg Gly Arg Gly Arg Thr Val Tyr Asn Thr Phe Arg Ala Ala Pro
        275                 280                 285
```

```
Pro Pro Pro Ile Pro Ala Tyr Gly Gly Val Val Tyr Pro Gly Trp Ile
    290             295                 300

Leu Trp Cys Arg His Leu Trp Trp Leu Cys Cys Ile Pro Leu Arg Pro
305             310             315                 320

Ala Tyr Pro Cys His Cys Arg Cys Leu Gln
                325             330
```